United States Patent [19]
Lin et al.

[11] Patent Number: 5,783,248
[45] Date of Patent: Jul. 21, 1998

[54] PROCESS FOR PRODUCING A BIOCERAMIC COMPOSITE MATERIAL CONTAINING NATURAL BONE MATERIAL ON AN ALUMINA SUBSTRATE

[75] Inventors: Ruey-Mo Lin; Nan-Chung Wu; Kuang-Hsing Liu, all of Tainan, Taiwan

[73] Assignee: National Science Council of R.O.C., Taipei, Taiwan

[21] Appl. No.: 519,935

[22] Filed: Aug. 28, 1995

[51] Int. Cl.$^6$ ............................................. B05D 3/00
[52] U.S. Cl. .................. 427/2.27; 477/314; 477/376.2; 477/419.3
[58] Field of Search .................. 427/2.27, 376.2, 427/419.3, 314

[56] References Cited

U.S. PATENT DOCUMENTS

| | | | |
|---|---|---|---|
| 4,847,163 | 7/1989 | Shimamune et al. | 428/469 |
| 4,871,578 | 10/1989 | Adam et al. | 427/2 |
| 4,878,914 | 11/1989 | Miwa et al. | 623/16 |
| 4,965,088 | 10/1990 | Shimamune et al. | 427/2 |
| 4,983,182 | 1/1991 | Kijima et al. | 623/16 |
| 4,988,362 | 1/1991 | Toriyama et al. | 623/66 |
| 5,077,079 | 12/1991 | Kawamura et al. | 427/2 |

OTHER PUBLICATIONS

Yokogawa et al., "Tricalsium Phosphate Coating on Zirconia by Using Calcium Metaphosphate and Tetracalcium Phosphate", Journal of The Ceramic Society of Japan, 99(3):211–214 (1991).

*Primary Examiner*—Benjamin Utech
*Attorney, Agent, or Firm*—Finnegan, Henderson, Farabow, Garrett & Dunner

[57] ABSTRACT

A process is provided for producing a bioceramic composite in which an alumina based ceramic substrate is coated with an intermediate calcium pyrophosphate layer to cement a porous calcium phosphate material to the alumina based ceramic substrate. In one aspect of the invention, the porous calcium phosphate material is a porous lattice made from natural bone. A bioceramic composite which includes an alumina-based ceramic substrate, an intermediate calcium pyrophosphate layer and a porous natural bone material bonded to the intermediate calcium pyrophosphate layer is also disclosed.

9 Claims, 10 Drawing Sheets

Al₂O₃  10μm

Al₂O₃  10μm

Al₂O₃  40μm

250μm

250μm

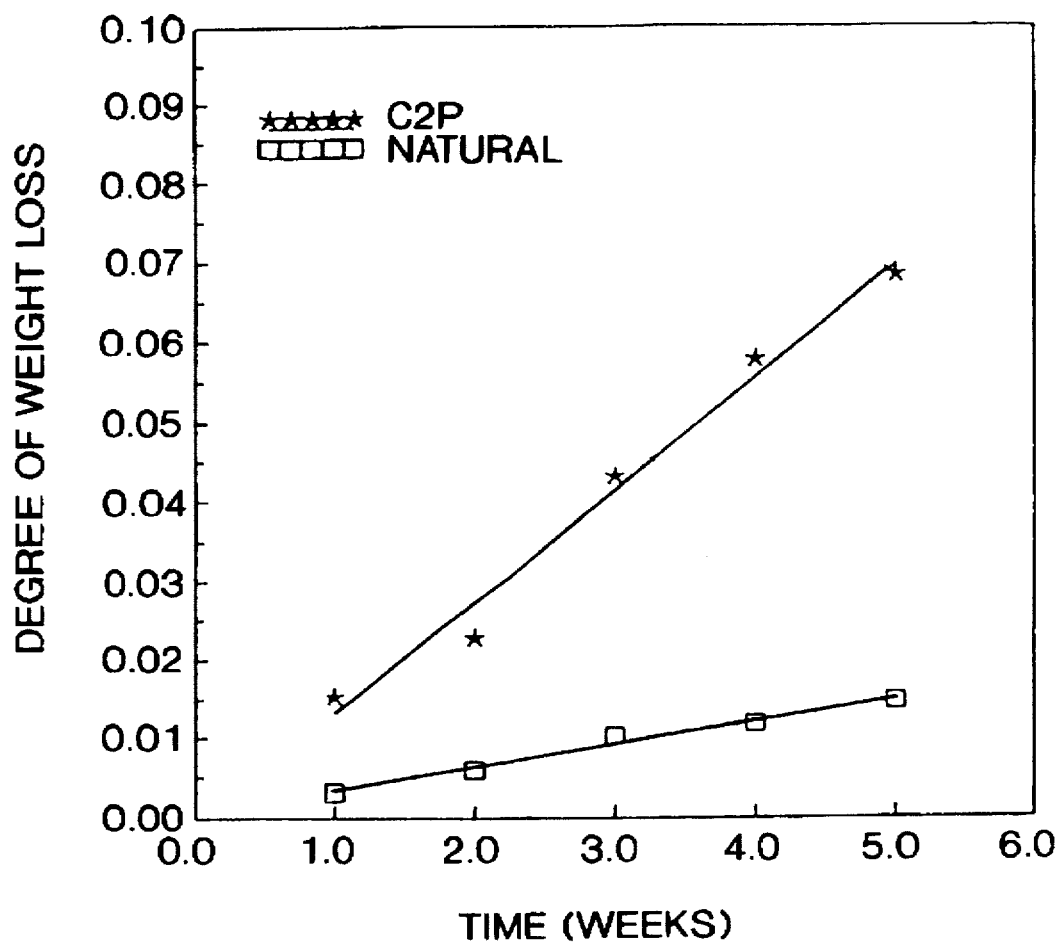
F I G. 15

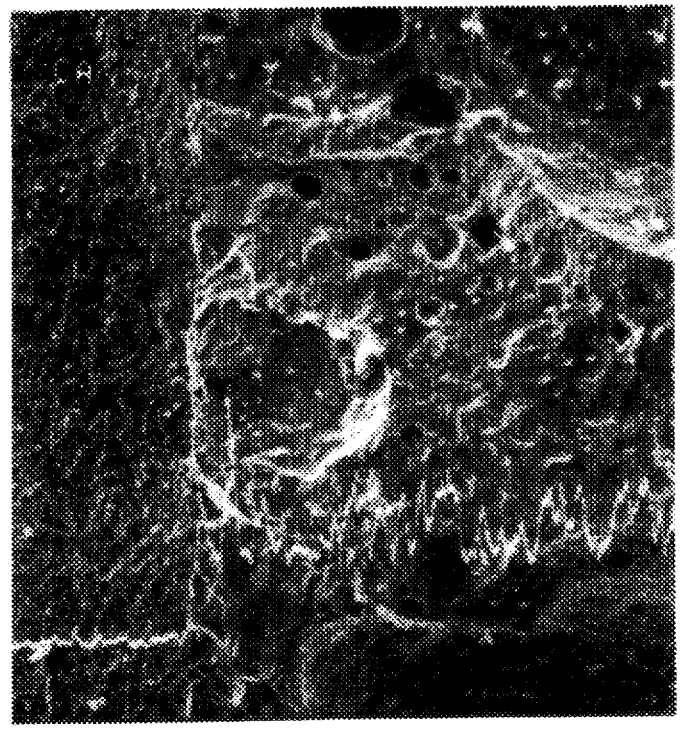
F I G. 16
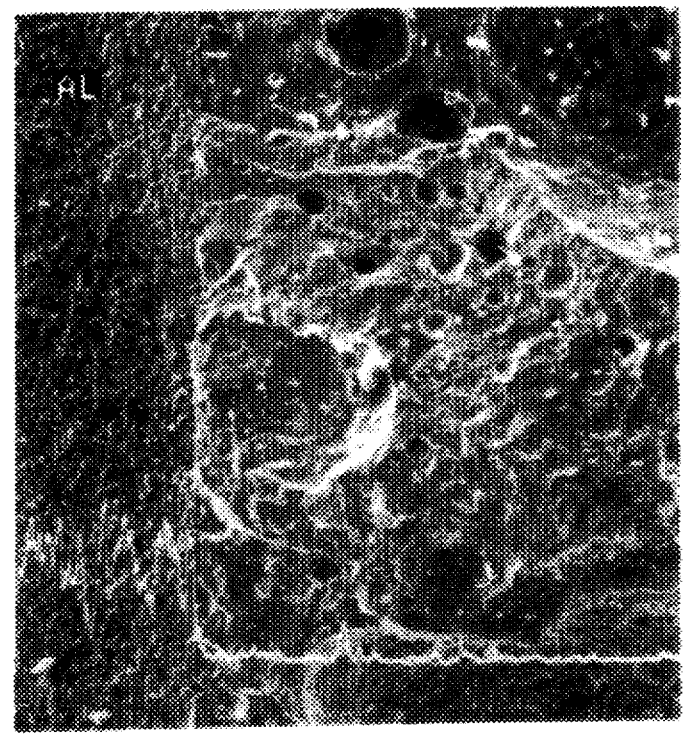
F I G. 17

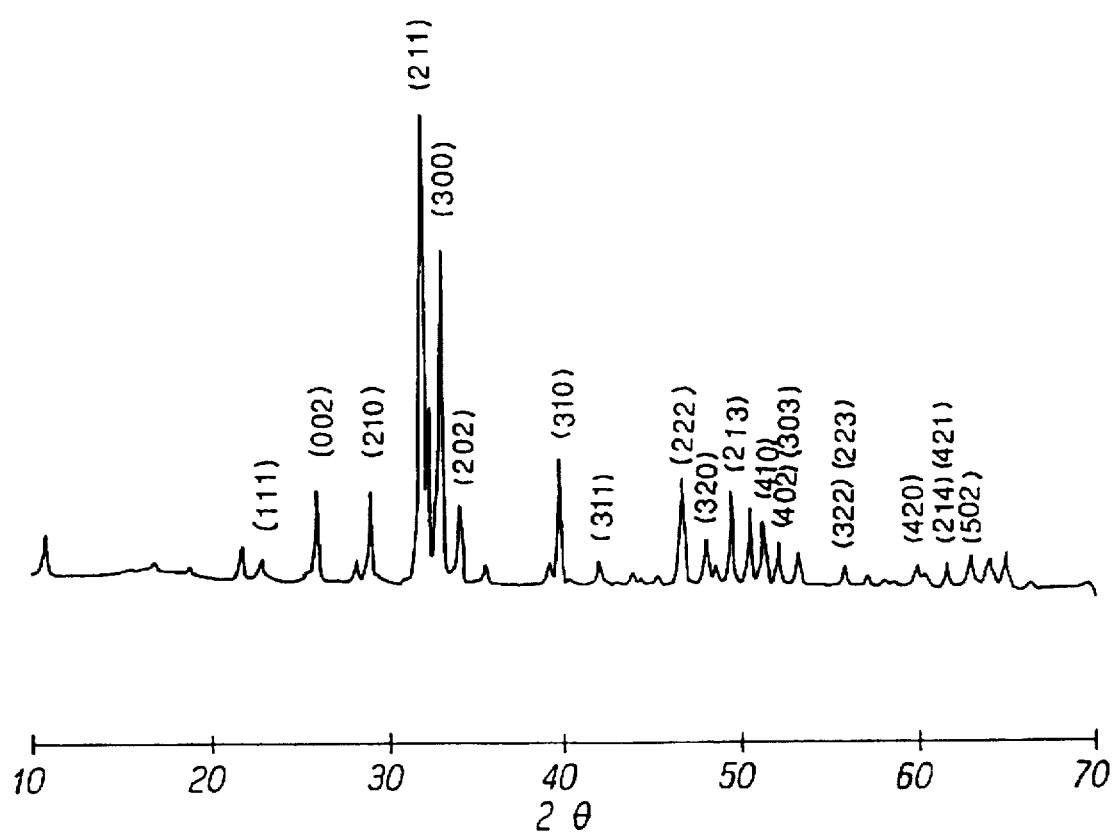
F I G. 20

PROCESS FOR PRODUCING A BIOCERAMIC COMPOSITE MATERIAL CONTAINING NATURAL BONE MATERIAL ON AN ALUMINA SUBSTRATE

BACKGROUND OF THE INVENTION

1. Field of the Invention

This invention relates to a bioceramic composite and a process of producing a bioceramic composite, and particularly to a bioceramic composite having an alumina based ceramic substrate and an intermediate calcium phosphate layer to firmly cement to the substrate a porous calcium phosphate material for the ingrowth of natural bone.

2. Description of the Related Prior Art

It has been known to use biocompatible calcium phosphate materials such as hydroxyapatite and β-tricalcium phosphate for prostheses. Such materials are, however, not satisfactory in practice due to their low mechanical strength. Many techniques have been developed heretofore to produce composite materials by using such biocompatible materials for coating substrates made of mechanically strong materials such as metals or ceramics.

For example, U.S. Pat. Nos. 4,965,088 and 4,847,163 disclose a calcium phosphate-coated composite material which comprises a metallic substrate, a coating layer of calcium phosphate and an intermediate oxide layer to firmly bond the coating layer to the substrate. A journal, namely, "Journal of the Ceramic Society of Japan 99(3)211–214 (1991)" discloses a tricalcium phosphate (β-TCP) coating formed on a high strength sintered zirconia substrate. Calcium metaphosphate is used as an interlayer, and the β-TCP layer is formed by heating a mixed slurry of calcium metaphosphate and tetracalcium phosphate which is applied on the interlayer.

Alumina has been used as a substitute for artificial hard tissue due to its bioinert property and satisfactory mechanical strength. Attempts have been made by the inventor of the present invention to form a layer of biocompatible porous material such as β-tricalcium phosphate on a sintered alumina substrate. The results, however, have been found unsuccessful because β-tricalcium phosphate has a poor bonding with the alumina substrate.

SUMMARY OF THE INVENTION

An object of the invention is to provide a bioceramic composite having an alumina based ceramic substrate and a calcium phosphate material which can be firmly bonded to an alumina based ceramic substrate.

Another object of the invention is to provide a bioceramic composite in which an alumina based ceramic substrate holds firmly a porous calcium phosphate material for ingrowth of natural bone.

a further object of the invention is to provide a process through which a porous calcium phosphate material can be firmly cemented to an alumina based ceramic substrate.

According to one aspect of the invention, a bioceramic composite comprises an alumina based ceramic substrate, an intermediate calcium pyrophosphate ($C_2P$) layer on the alumina based ceramic substrate, and a porous calcium phosphate material cemented to the alumina based ceramic substrate by the intermediate calcium pyrophosphate layer as a cementing layer. Advantageously, the porous calcium phosphate material is a hydroxyapatite material obtained from a natural bone material.

According to another aspect of the invention, a process of producing a bioceramic composite which comprises forming on an alumina based ceramic substrate with an intermediate layer consisting essentially of calcium pyrophosphate ($C_2P$) and cementing a porous calcium phosphate material to the alumina based ceramic substrate by using the intermediate calcium pyrophosphate layer as a cementing layer. The intermediate calcium pyrophosphate may be formed from calcium metaphosphate (CP) and other calcium phosphate materials that can yield a calcium pyrophosphate phase upon being sintered on the alumina substrate. On the other hand, the porous calcium phosphate material is prepared by heating a natural bone material.

BRIEF DESCRIPTION OF THE DRAWINGS

The above and other objects, features, and advantages of the present invention will be better understood from the following description taken in conjunction with the accompanying drawings, in which:

FIGS. 15 is a diagram showing the weight loss of composite samples vs. the times of immersing the composite samples in the Ringer's solution;

FIGS. 16 to 18 are photomicrographs under an EDS element analysis of the natural bone containing composite according to the present invention;

FIG. 20 is an X-ray diffraction diagram of the natural bone material after heating to 700° C.

DETAILED DESCRIPTION OF THE PREFERRED EMBODIMENTS

Preparation of an Alumina Based Ceramic Substrate

A slurry was prepared in a conventional manner by milling a micro particle alumina powder of industrial grade together with a binder, a dispersant, water, etc. Samples were made by forming the cake obtained from the slurry. After drying, the samples were sintered to form dense alumina ceramic substrate samples.

Preparation of Calcium Metaphosphate (CP)

0.05% by mole of calcium carbonate and 0.1% by mole of ammonium biphosphate were wet milled (using an alcohol solution) for 4–6 hr in a ball mill containing alumina milling balls. After the resulting slurry is filtered (100 mesh), it was heated to evaporate the alcohol solution and then dried in an oven at 70° C. for 24 hr.

The dried powder was heated in a high temperature furnace under atmosphere at 800° C. for 8 hr. Afterwards, the resultant foam-like calcium metaphosphate was powdered. From an X-ray diffraction analysis, it was confirmed that the heated product is calcium metaphosphate.

Coating the Alumina Substrate with Calcium Metaphosphate (First Coating)

Aqueous calcium metaphosphate coating compositions were prepared by mixing calcium metaphosphate powder with deionized water in the presence of a suitable dispersant at varying solid concentrations. An example of the dispersant used in the invention is a product of Nippon Chu Kyo Oil Co., Ltd., under the trade name of Selna D305 and the used amount of the Selna D305 product was 0.2%–0.6% based on the total weight of the composition.

Figure 1:
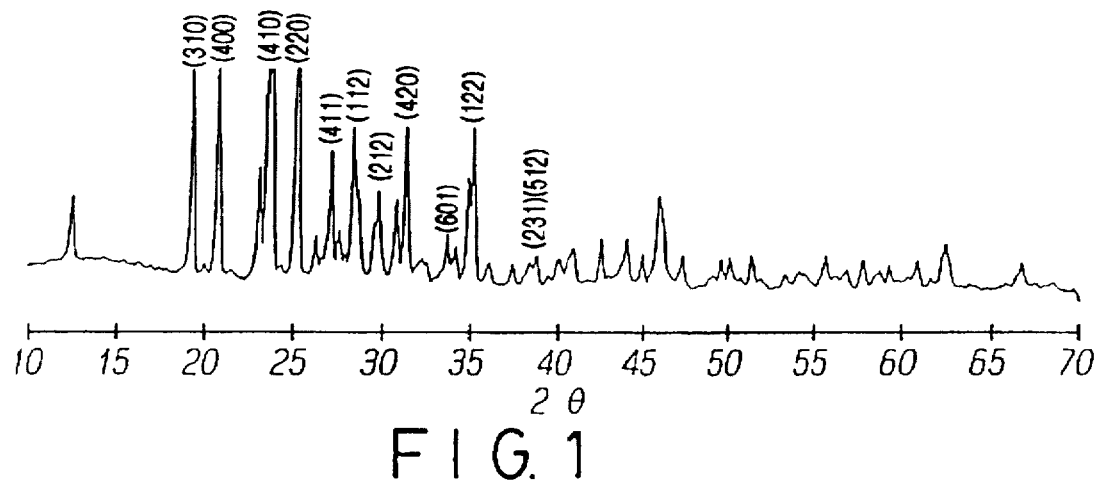
FIGS. 1, 2 and 3 are diagrams of X-ray diffraction analysis of the first coating compositions formed on alumina substrate samples which were sintered at 950° C., 1000° C. and 1050° C. respectively.
Figure 2:
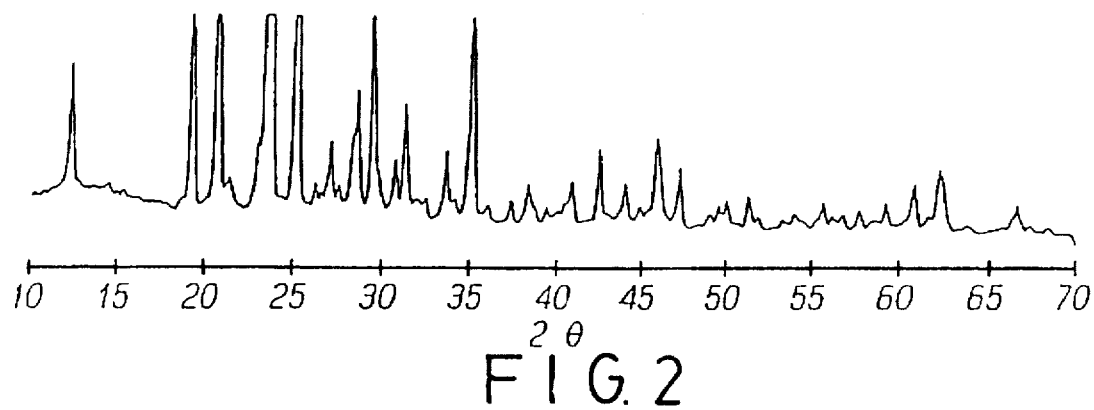
Figure 3:
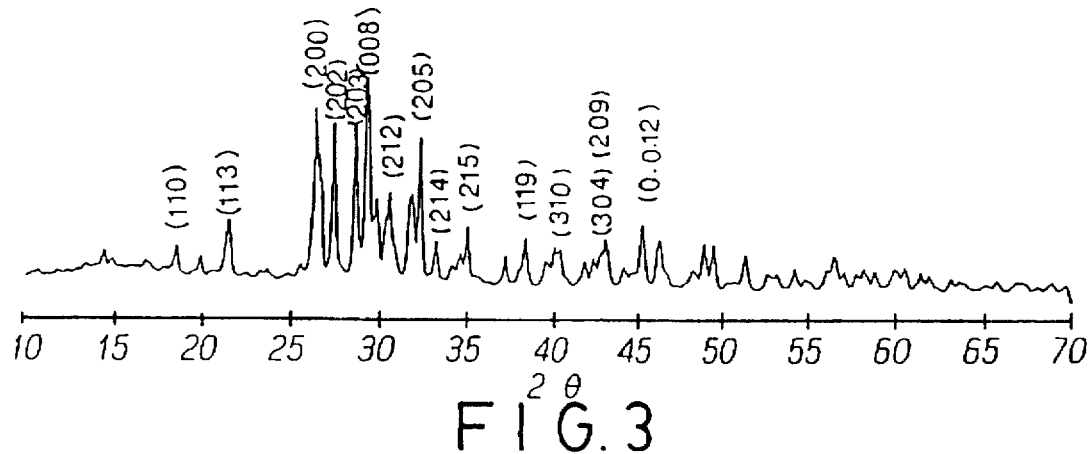

Alumina substrate samples were coated by dipping in the calcium metaphosphate coating compositions. Each coated substrate was then sintered so as to achieve a high bonding between the coating layer and the substrate. The sintering temperature used in the invention was higher than 950° C. FIGS. 1, 2 and 3 are directed to an X-ray diffraction analysis of the samples which were sintered at 950° C., 1000° C. and 1050° C. for 40 min at a temperature increment rate of 20° C./min. At 950° C., calcium metaphosphate did not adhere to the alumina substrate since the sintering temperature was lower than the melting point of calcium metaphosphate. When the sintering temperature was 1000° C., the calcium metaphosphate phase layer was tightly bonded to the alumina substrate. When the sintering temperature was increased to 1050° C., a β-calcium pyrophosphate phase was formed at the surface region of the sintered product. With a prolonged retention time at said temperature, the calcium metaphosphate entirely transformed to a β-calcium pyrophosphate phase. It was found that β-calcium pyrophosphate phase could be reproduced more readily than the calcium metaphosphate phase.

Coating the Coated Substrate with a Second Coating Composition containing calcium metaphosphate plus hydroxyapatite 0.1% by mol of $CaCO_3$ and 0.05% by mol of $NH_4H_2PO_4$ were milled for 5 hr in a ball mill containing alumina milling balls in the presence of an alcohol solution. After the mixture was dried in an oven, the dried powder was heated to 1400° C. under atmospheric pressure and maintained at said temperature for 8 hr. The resulting product is tetracalcium phosphate or hydroxyapatite. Hydroxyapatite was mixed with the calcium metaphosphate obtained as mentioned above in a ratio of 1:2 in a ball mill in the presence of an alcohol. The mixture was dried and ground to form a powder. The powder was then mixed with deionized water to form slurry compositions having different solid concentrations.

The resultant slurry compositions were used as a second coating composition to be applied on the alumina substrate samples already formed with layers of calcium pyrophosphate (the first coating) having different film thicknesses. The so coated composites were then sintered at different temperatures and the resultant products were studied through an X-ray diffraction analysis. It was found that a β-tricalcium phosphate phase or a β-calcium pyrophosphate phase was formed in the second coating layer depending on the film thickness of the first coating layer and the sintering temperatures. It was also found that, whenever a poor bonding was formed between the second coating and the coated alumina substrate, a β-tricalcium phosphate phase was found in the second coating layer, and that, whenever there is a strong bonding between the substrate and the second coating layer, a β-calcium pyrophosphate phase was recognized in the second coating layer.

Figure 4:
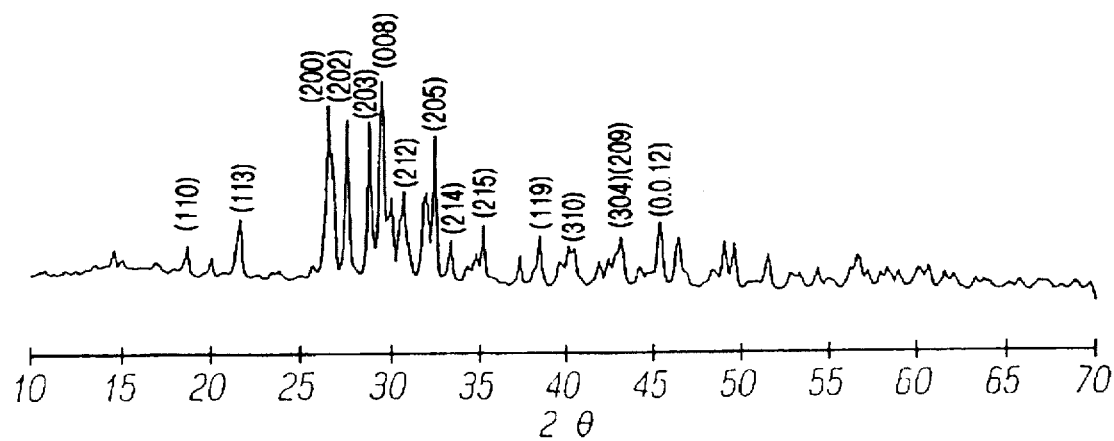
FIGS. 4, 5 and 6 are diagrams of X-ray diffraction analysis of the second coating compositions formed on the alumina substrate samples which were sintered at 1150° C., 1200° C. and 1250° C., respectively.
Figure 5:
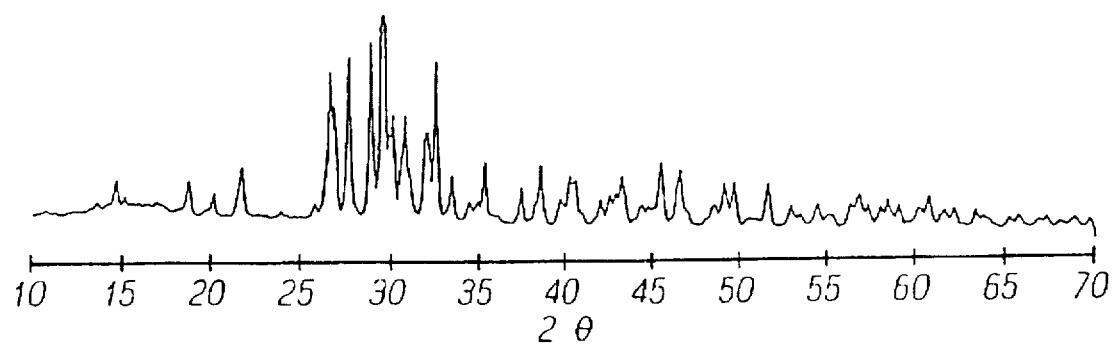
Figure 6:
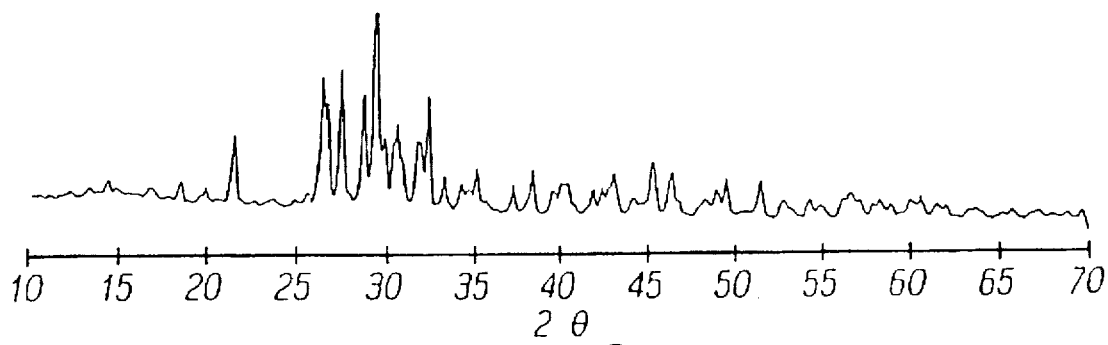

FIGS. 4, 5 and 6 are directed to an X-ray diffraction analysis of the samples which were successfully formed with a β-calcium pyrophosphate phase when sintered at 1150° C., 1200° C. and 1250° C. for 40 min at a temperature increment rate of 20° C./min.

Additional experiments were conducted by following the procedure of the above-mentioned second coating using the second coating compositions with the calcium metaphosphate to hydroxyapatite ratios of 1:3 and 1:4. From a study of the results of these experiments, it has been discovered that the calcium phosphate material that can be formed firmly or reproduced readily on an alumina ceramic substrate is the β-calcium pyrophosphate phase.

The bonding strength between the alumina ceramic substrate and the β-calcium pyrophosphate layer and between the alumina ceramic substrate and the calcium metaphosphate layer was determined based on an indentation method using AKASHI, MVK-E Hardness Tester with a load of 300 g. The tests have manifested that the bonding between the β-calcium pyrophosphate layer and the alumina ceramic is very strong, though lower than that formed between the calcium metaphosphate layer and the alumina ceramic substrate.

The thickness of the first coating formed directly on the alumina substrate should be greater than 30 μm, preferably 30 μm–150 μm, so as to be an effective cementing layer to hold an additional layer of calcium phosphate material on the alumina substrate. Specifically, if the thickness of the first coating is less than 30 μm, β-tricalcium phosphate phase will exist in the second coating layer so that the second coating layer can not be held firmly on the alumina substrate. If the thickness is greater than 30 μm, the calcium pyrophosphate phase formed in the first coating would react with the β-tricalcium phosphate phase formed in the second coating, thereby converting the β-tricalcium phosphate phase into a β-calcium pyrophosphate which can be bonded firmly to the alumina substrate.

Figure 7:
FIGS. 7, 8 and 9 are photomicrographs under a scanning electron microscope of the alumina substrates together with the first coating compositions having solid concentrations of 20%, 40% and 60%, respectively and sintered at 1000° C.
Figure 8:
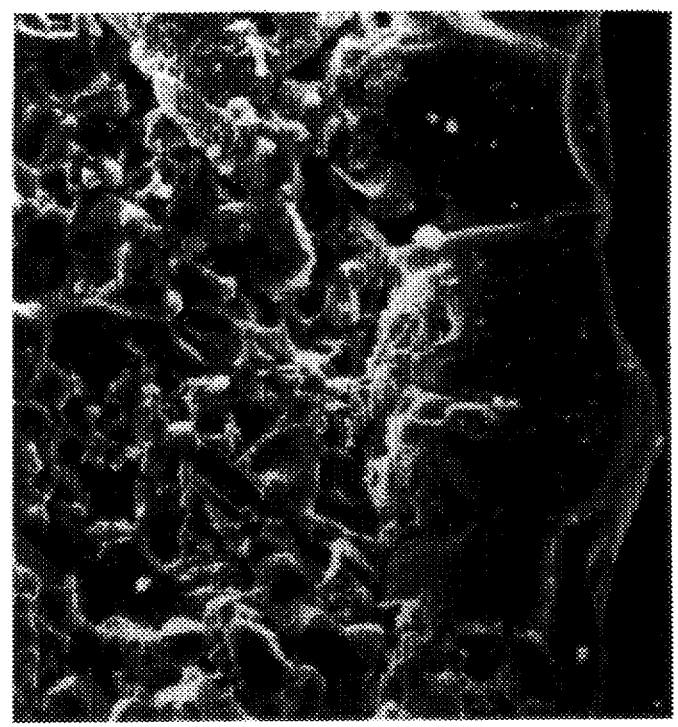
Figure 9:

The thickness of the first coating formed on the alumina substrate may be controlled by using a coating slurry having an appropriate solid concentration. When the solid concentration of the first coating composition is 20–60 wt %, the resulting film will have a thickness of 20–180 μm. FIGS. 7 to 9 show that the thicknesses of the films on the alumina substrate are 22 μm, 30 μm and 180 μm, respectively, when the solid concentrations of the first coating compositions are 20%, 40% and 60% and the compositions are sintered at 1000° C.

In another aspect of the invention, calcium pyrophosphate formed on an alumina substrate is used as an intermediate cementing layer to hold a porous calcium phosphate material on the alumina substrate for the ingrowth of natural bone. Preferably, natural bone is used as a source to make porous lattices of calcium phosphate material. The porous lattices soaking in the slurry of calcium metaphosphate can be bonded to the calcium pyrophosphate coated alumina substrate by heating to a temperature of 1000° C.–1250° C.

EXAMPLE

Alumina substrate samples were prepared from a micro particle alumina powder of industrial grade and sintered at 1400°–1450° C. for 3–4 hours. The rate of heating was 2°–4° C./min.

0.05% by mole of calcium carbonate and 0.1% by mole of ammonium biphosphate were wet milled (using an alcohol solution) for 4–6 hr in a ball mill containing alumina milling balls. After the resulting slurry was filtered (100 mesh), it was heated to evaporate the alcohol solution and then dried in an oven at 70° C. for 24 hr.

The dried lumps were heated in a high temperature furnace under atmosphere at 800° C. for 8 hr. The resultant foam-like calcium metaphosphate was powdered and formulated with deionized water to form a coating slurry of 50% solid concentration by using 0.4% by weight of the dispersant produced by Nippon Chu Kyo k.k. under the trade name of Selna D305.

The alumina substrate samples were dipped into the 50% calcium metaphosphate slurry and then sintered at 1050° C. for 40 min with a temperature increment rate of 20° C./min to form a β-calcium pyrophosphate phase. The thickness of the film is about 60 μm.

Figure 10:
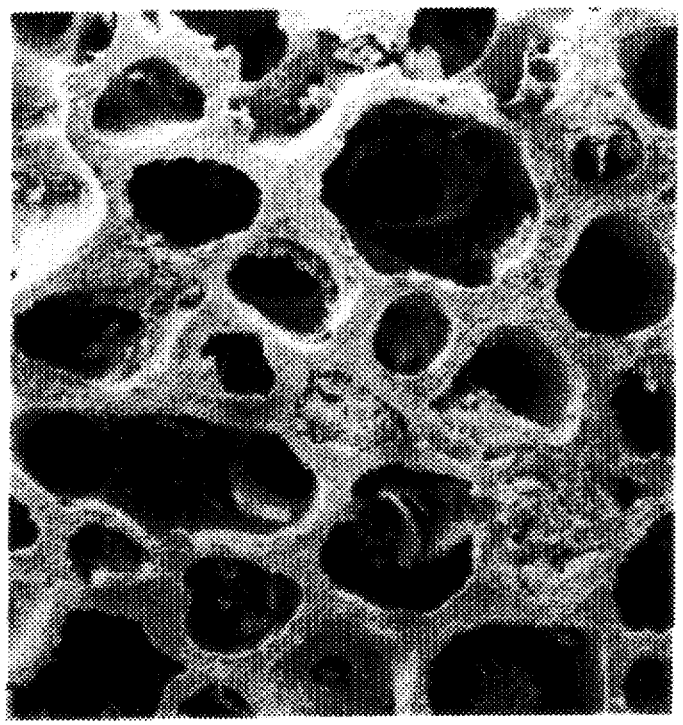
FIGS. 10 and 11 are photomicrographs under a scanning electron microscope of the natural bone material before sintering and after sintering.
Figure 11:
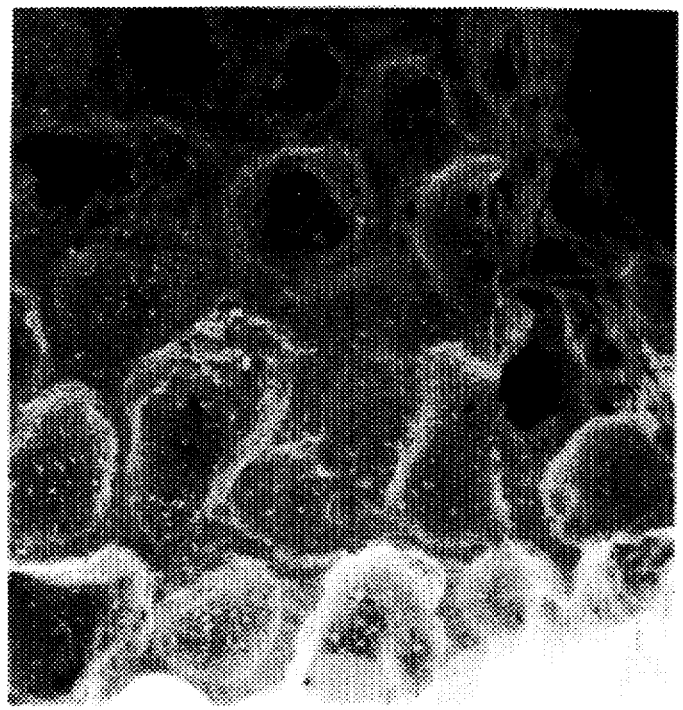

A natural bone body (porcine vertebral body) was sectioned into slices having 1-2 mm in thickness. The slices were heated at 700° C. for 8 hr thereby obtaining porous lattice samples of hydroxyapatite. The X-ray diffraction diagram shown in FIG. 20 confirms that the porous lattice is hydroxyapatite. The porous lattice samples were dipped in a coating composition containing 20% by weight of calcium metaphosphate and then placed on the above-mentioned coated alumina substrate samples. The alumina substrate samples so coated were then sintered again at 1100° C. for 40 min with a heat increment rate of 20°C./min to form composite samples. FIGS. 10 and 11 are photographs (magnified 4-times) of the porous lattice of the natural bone material before and after sintering. The porous lattice has a pore diameter distribution of 0.15 mm–0.70 mm. After sintering, β-calcium pyrophosphate is formed in the pores of the sintered bone.

Figure 12:
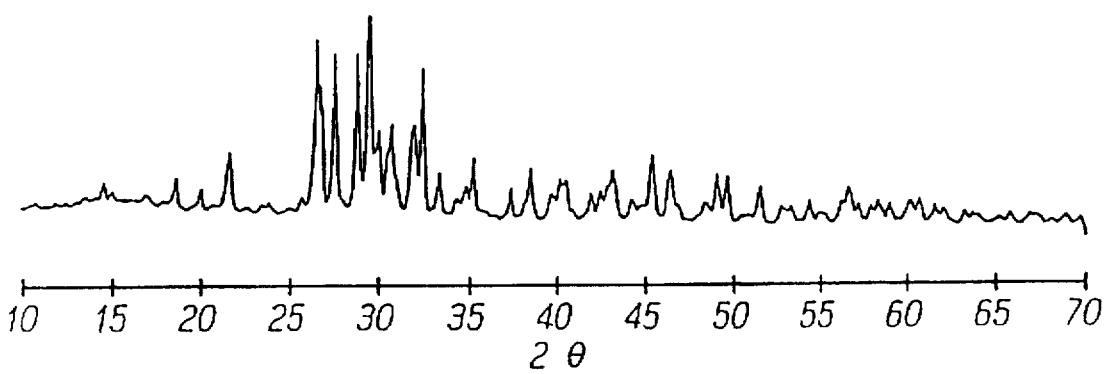
FIGS. 12 to 14 are X-ray diffraction diagrams of the composite samples before and after immersion in Ringer's solution.
Figure 13:
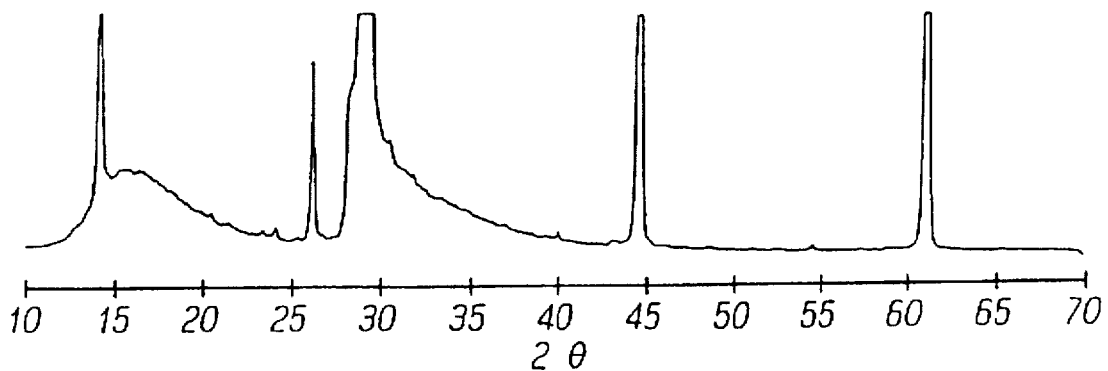
Figure 14:
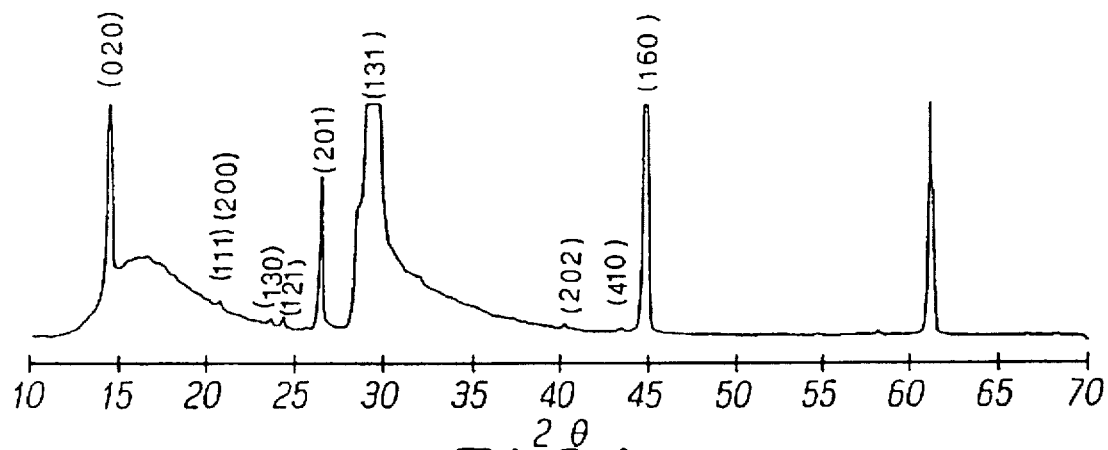

The composite samples were put into a Ringer's solution so as to evaluate the possible dissolution characteristics of the composite samples in a body fluid. The samples were taken out from the solution after one, two, three, and four weeks respectively and analyzed by X-ray diffraction. FIG. 12 shows that the layer on the alumina substrate is β-calcium pyrophosphate before it is put into the Ringer's solution. FIGS. 13 and 14 show that β-calcium pyrophosphate transforms to σ-calcium pyrophosphate when the composite samples are removed from the Ringer's solution after one and four weeks, respectively.

TABLE I

| Time<br>Wt Loss | 1 Week<br>(wt %) | 2 Week<br>(wt %) | 3 Week<br>(wt %) | 4 Week<br>(wt %) | 5 Week<br>(wt %) |
| --- | --- | --- | --- | --- | --- |
| $Al_2O_3$—$C_2P$<br>($C_2P$) | 0.0154 | 0.0227 | 0.0432 | 0.0578 | 0.0682 |
| $Al_2O_3$—$C_2P$—<br>Natural bone | 0.0032 | 0.0059 | 0.0102 | 0.0118 | 0.0148 |

Figure 18:
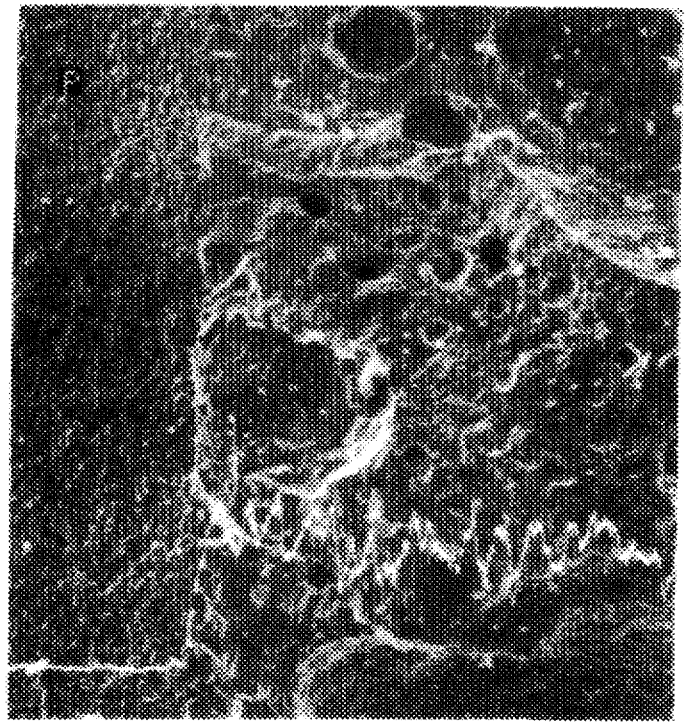
Figure 19:
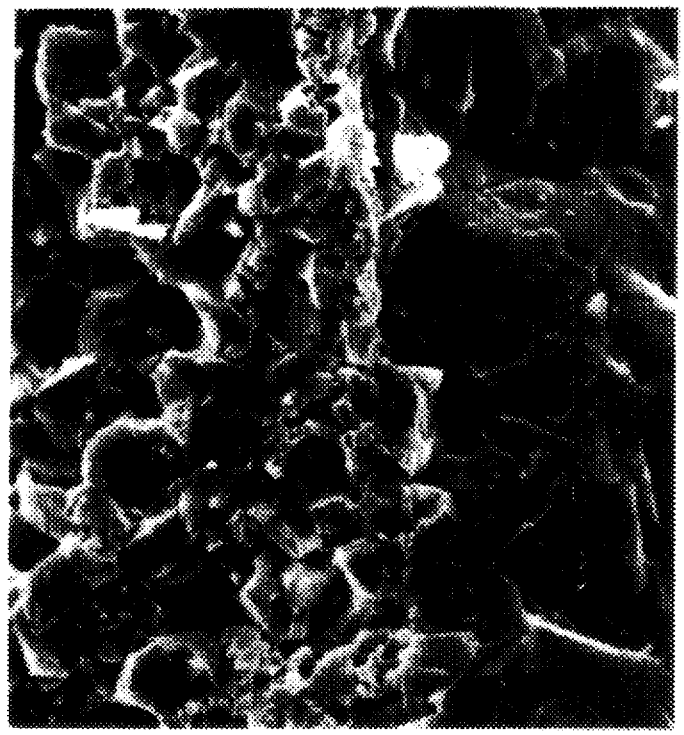
FIGS. 19 is a photomicrograph under a scanning electron microscope of the natural bone containing composite according to the present invention.

Table 1 and FIG. 15 manifest the weight losses of two samples measured after they are taken out from the Ringer's solution. It can be appreciated that the sample which does not use natural bone is more reactive towards the Ringer's solution. In other words, the sample containing the natural bone material is not readily dissolved by the Ringer's solution. The picture of an SEM analysis shown in FIG. 19 shows that a good bonding is produced between the porous lattice of natural bone material and the alumina substrate. From FIGS. 16 to 18, it can be seen that no significant diffusion behavior occurs in relation to aluminum, calcium and phosphor elements in the resulting composite, respectively.

Although some preferred embodiments have been described, many modifications and variations may be made thereto in the light of the above teachings. It is therefore to be understood that with the scope of the appended claims, the invention may be practiced otherwise than as specifically described.

We claim:

1. A process for producing a bioceramic composite comprising:

a) preparing an alumina based ceramic substrate;

b) forming on said substrate a layer of calcium phosphate material;

c) heating a natural bone material in an amount sufficient to obtain a porous natural bone material;

d) coating said porous natural bone material with a calcium phosphate material;

e) placing said coated porous natural bone material on said layer of calcium phosphate material on said substrate to form a composite and thereafter sintering said composite to bond said porous natural bone material to said alumina based ceramic substrate.

2. The process of claim 1, wherein said layer of calcium phosphate material is a layer of calcium pyrophosphate and is formed on the substrate by applying to the substrate a coating composition consisting essentially of calcium metaphosphate and then sintering the coated substrate to form a layer of calcium pyrophosphate on said substrate.

3. The process of claim 2, wherein the calcium pyrophosphate layer has a thickness of from 30 to 150 μm.

4. The process of claim 1, wherein the natural bone material is heated at about 700° C.

5. The process of claim 4, wherein the natural bone material is heated at about 700° C. for eight hours.

6. The process of claim 1, wherein the porous natural bone material is coated with a composition consisting essentially of calcium metaphosphate.

7. The process of claim 1, wherein the composite of the alumina based ceramic substrate and the coated porous natural bone material is sintered at a temperature of from 1000° to 1250° C.

8. The process of claim 7, wherein the composite is sintered at a temperature of about 1100° C.

9. A process for producing a bioceramic composite comprising:

a) preparing an alumina based ceramic substrate;

b) heating a natural bone material in an amount sufficient to obtain a porous natural bone material;

c) joining said porous natural bone material to said alumina based ceramic substrate with a calcium phosphate material to form a composite and thereafter sintering said composite to bond said porous natural bone material to said alumina based ceramic substrate.

* * * * *